United States Patent
Braun et al.

(10) Patent No.: US 9,072,684 B2
(45) Date of Patent: *Jul. 7, 2015

(54) CATIONIC THICKENERS, FREE OF OIL AND SURFACTANTS, METHOD FOR PREPARING SAME AND COMPOSITION CONTAINING SAME

(75) Inventors: Olivier Braun, Castres (FR); Paul Mallo, Croissy-sur-Seine (FR)

(73) Assignee: SOCIETE D'EXPLOITATION DE PRODUITS POUR LES INDUSTRIES CHIMIQUES SEPPIC, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/878,594

(22) PCT Filed: Nov. 29, 2011

(86) PCT No.: PCT/FR2011/052808
§ 371 (c)(1),
(2), (4) Date: Apr. 10, 2013

(87) PCT Pub. No.: WO2012/072943
PCT Pub. Date: Jun. 7, 2012

(65) Prior Publication Data
US 2013/0197177 A1   Aug. 1, 2013

(30) Foreign Application Priority Data
Dec. 1, 2010  (FR) ...................................... 10 59950

(51) Int. Cl.
| | |
|---|---|
| C08F 220/26 | (2006.01) |
| C08F 218/02 | (2006.01) |
| A61K 8/81 | (2006.01) |
| C08F 220/64 | (2006.01) |
| C08F 220/62 | (2006.01) |
| C08F 220/06 | (2006.01) |
| C08F 220/28 | (2006.01) |
| C08F 220/60 | (2006.01) |
| A61Q 5/00 | (2006.01) |
| A61Q 5/12 | (2006.01) |
| A61K 8/86 | (2006.01) |
| C08F 226/02 | (2006.01) |
| C08F 20/06 | (2006.01) |
| C08F 20/02 | (2006.01) |
| C08F 20/54 | (2006.01) |
| C08F 20/04 | (2006.01) |
| C08F 20/64 | (2006.01) |
| C08F 20/62 | (2006.01) |
| C08F 22/38 | (2006.01) |

(Continued)

(52) U.S. Cl.
CPC ............... *A61K 8/8152* (2013.01); *C08F 20/06* (2013.01); *C08F 20/02* (2013.01); *C08F 20/54* (2013.01); *C08F 20/04* (2013.01); *C08F 20/64* (2013.01); *C08F 20/62* (2013.01); *C08F 2800/10* (2013.01); *C08F 22/38* (2013.01); *C08F 220/64* (2013.01); *C08F 22/02* (2013.01); *C08F 220/02* (2013.01); *C08F 220/62* (2013.01); *C08F 220/54* (2013.01); *C08F 220/04* (2013.01); *C08F 220/06* (2013.01); *C08F 220/28* (2013.01); *C08F 220/60* (2013.01); *A61Q 5/002* (2013.01); *A61Q 5/12* (2013.01); *A61K 8/86* (2013.01); *C08F 226/02* (2013.01)

(58) Field of Classification Search
CPC .......... C08F 20/02; C08F 20/04; C08F 20/06; C08F 20/62; C08F 20/64; C08F 20/54; C08F 220/02; C08F 220/04; C08F 220/06; C08F 220/62; C08F 220/64; C08F 220/54; C08F 22/02; C08F 22/38; C08F 226/02; C08F 2800/10
USPC ........ 526/312, 318.1, 318.2, 318.3, 911, 910, 526/923, 932
See application file for complete search history.

(56) References Cited

U.S. PATENT DOCUMENTS 4,517,351 A * 5/1985 Szymanski et al. ............ 527/312
4,737,541 A * 4/1988 Stavenger et al. ............. 524/547

(Continued)

FOREIGN PATENT DOCUMENTS

| EP | 0 503 853 | 9/1992 |
|---|---|---|
| EP | 1 449 862 | 8/2004 |

(Continued)

OTHER PUBLICATIONS

International Search Report dated Apr. 11, 2012 in corresponding PCT application.

*Primary Examiner* — Ling Choi
*Assistant Examiner* — David L Miller
(74) *Attorney, Agent, or Firm* — Young & Thompson

(57) ABSTRACT

Polyelectrolyte resulting from polymerization, for 100 mol %, of: a) a molar ratio ≥50% and ≤99% of monomer units originating from at least one cationic monomer; b) a molar ratio >1% and ≤50% of monomer units originating from at least one monomer including a fully or partially salified free weak acid function; c) optionally a molar ratio >0 mol % and ≤5 mol % of monomer units originating from at least one monomer of formula A-C(=O)—O—[(CH$_2$—CH(R$_1$)—O]$_n$—R (I), where n is, independently, a number from 1 to 50, A is a monovalent unsaturated aliphatic radical having 2 to 6 carbon atoms, R$_1$ is a hydrogen atom, a methyl radical, or an ethyl radical, and R is a linear or branched, saturated or unsaturated aliphatic hydrocarbon radical having 8 to 30 carbon atoms; and d) optionally a molar ratio >0% and ≤1% of a diethylene or polyethylene cross-linking monomer.

13 Claims, No Drawings

(51) Int. Cl.
*C08F 22/02* (2006.01)
*C08F 220/02* (2006.01)
*C08F 220/54* (2006.01)
*C08F 220/04* (2006.01)

(56) References Cited

U.S. PATENT DOCUMENTS

| | | | |
|---|---|---|---|
| 4,806,345 A | 2/1989 | Bhattaccharyya | |
| 5,004,598 A | 4/1991 | Lochhead et al. | |
| 5,100,660 A | 3/1992 | Hawe et al. | |
| 5,879,679 A * | 3/1999 | Taylor et al. | 424/178.1 |
| 6,136,305 A | 10/2000 | Michel-Lecocu et al. | |
| 6,197,287 B1 | 3/2001 | Mallo et al. | |
| 6,346,239 B1 | 2/2002 | Mallo et al. | |
| 7,015,279 B2 * | 3/2006 | Braun et al. | 524/815 |
| 2003/0172472 A1 | 9/2003 | Laurent | |
| 2004/0238138 A1 * | 12/2004 | Ishizaki et al. | 162/164.6 |
| 2008/0312343 A1 * | 12/2008 | Braun et al. | 514/772.3 |
| 2009/0308553 A1 | 12/2009 | Souzy et al. | |
| 2010/0280169 A1 * | 11/2010 | Destarac | 524/555 |
| 2013/0123372 A1 * | 5/2013 | Dobrawa et al. | 514/772.6 |

FOREIGN PATENT DOCUMENTS

| | | |
|---|---|---|
| FR | 2 810 882 | 1/2002 |
| FR | 2 900 411 | 11/2007 |
| JP | 10264497 A * | 10/1998 |
| WO | 2006/123038 | 11/2006 |
| WO | 2009/059887 | 5/2009 |

* cited by examiner

CATIONIC THICKENERS, FREE OF OIL AND SURFACTANTS, METHOD FOR PREPARING SAME AND COMPOSITION CONTAINING SAME

The subject of the invention is novel polymeric cationic thickeners, the process for preparing same and also the use thereof as a thickener and/or emulsifier.

The thickening of aqueous phases is generally carried out by incorporating therein hydrophilic polymers of all types, whether they are synthetic or of natural origin.

Among the polymers of natural origin, xanthan or guar gums are quite widely used. However, they have the conventional drawbacks of natural products, namely fluctuating quality and price.

Among the hydrophilic synthetic thickeners most widely used are polymers in the form of powders or of self-invertible inverse latexes. They are used in a wide pH range and are often well tolerated by human beings. Such compositions are described, for example, in the United States patents published under numbers U.S. Pat. No. 5,004,598, U.S. Pat. No. 6,197,287, U.S. Pat. No. 6,136,305 or U.S. Pat. No. 6,346,239 or in the European patent application published under number EP 0 503 853. These polymers are in the form of latex or of powder.

These polymers are anionic and are therefore essentially intended for thickening aqueous phases containing the various conventional constituents that can be found in topical formulations of the cosmetic, dermopharmaceutical or pharmaceutical industry. Mention will in particular be made of oils, surfactants (nonionic or anionic) also called emulsifiers, mineral salts and weak acids.

Certain formulations in particular intended for hair care contain cationic surfactants and/or cationic conditioning polymers. In this particular case, the thickeners made up of anionic polymers are not recommended for reasons obvious to those skilled in the art. Cationic thickening polymers such as those described in the United Stated patents published under numbers U.S. Pat. No. 4,806,345 and U.S. Pat. No. 5,100,660 are preferably used.

Although the latter behave satisfactorily in an acidic medium and they are compatible with cationic surfactants, they nevertheless lose their thickening capacity in electrolyte-rich formulations.

This problem has been partially solved by virtue of the polymers disclosed in the European patent application published under number EP 1 449 862.

Nevertheless, when they are in the form of inverse latexes, but also in the form of powders obtained by spray-drying said inverse latexes, these polyelectrolytes comprise not insignificant amounts not only of low-HLB surfactants necessary for the inverse-emulsion polymerization process to be carried out correctly, but also often of high-HLB surfactants termed inverters. However, the presence of such compounds can sometimes be an impediment for the cosmetic composition formulator. Furthermore, the presence of oils, even in a low amount as in the case of these powders, can generate a negative effect on the appearance of the final formulation, said aspect playing a definite role in the commercial success or failure of said formulation.

Consequently, the inventors have sought to develop electrolyte-resistant cationic thickening polymers free of any presence of oil or surfactants such as those mentioned above.

According to a first aspect, a subject of the invention is a linear, branched or crosslinked polyelectrolyte resulting from the polymerization, for 100 mol %:

a) of a molar proportion greater than or equal to 50% and less than or equal to 99% of monomeric units resulting from at least one cationic monomer, b) of a molar proportion greater than or equal to 1% and less than or equal to 50% of monomeric units resulting from at least one monomer comprising a free or partially or totally salified weak acid function, c) optionally of a molar proportion greater than 0% and less than or equal to 5 mol % of monomeric units resulting from at least one monomer of formula (I):

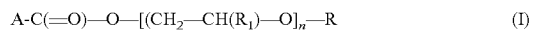

$$A\text{-}C(=O)\text{-}O\text{-}[(CH_2\text{-}CH(R_1)\text{-}O]_n\text{-}R \qquad (I)$$

in which n represents, independently, a number between 1 and 50, A represents an unsaturated aliphatic monovalent radical comprising from 2 to 6 carbon atoms, $R_1$ represents a hydrogen atom, a methyl radical or an ethyl radical and R represents a linear or branched, saturated or unsaturated hydrocarbon-based aliphatic radical comprising from 8 to 30 carbon atoms, and d) optionally of a molar proportion greater than 0% and less than or equal to 1% of a diethylene or polyethylene crosslinking monomer.

The term "branched polyelectrolyte" denotes a nonlinear polyelectrolyte which has pendant chains so as to obtain, when it is dissolved in water, a highly entangled state resulting in very high viscosities at low rate gradient.

The term "crosslinked polyelectrolyte" denotes a nonlinear polyelectrolyte which is in the form of a three-dimensional network that is water-insoluble but water-swellable and therefore results in the obtaining of a chemical gel.

The polyelectrolyte obtained by means of the process according to the invention can comprise crosslinked units and/or branched units.

The term "cationic monomer" denotes principally an aliphatic monomer comprising a quaternary ammonium function and at least one unsaturated carbon-carbon bond. Such a monomer is generally available in the form in particular of salts.

The term "salts" denotes more particularly halides, such as bromides, chlorides or iodides, of said monomers comprising a quaternary ammonium function. According to one particular aspect, a subject of the invention is the polyelectrolyte as previously defined, for which the monomeric units resulting from at least one cationic monomer result from the following quaternary ammonium salts:

N,N,N-trimethyl-3-[(2-methyl-1-oxo-2-propenyl)-amino] propanammonium salts;

N,N,N-trimethyl-3-[(1-oxo-2-propenyl)amino]propanammonium salts;

diallyldimethylammonium salts, or

N,N,N-trimethyl-2-[(2-methyl-1-oxo-2-propenyl)]ethanammonium salts;

and more particularly:

N,N,N-trimethyl-3-[(2-methyl-1-oxo-2-propenyl)amino] propanammonium chloride (MAMPTAC™);

N,N,N-trimethyl-3-[(1-oxo-2-propenyl)amino]propanammonium chloride (APTAC™);

diallyldimethylammonium chloride (DADMAC™), or

N,N,N-trimethyl-2-[(2-methyl-1-oxo-2-propenyl)]ethanammonium chloride (MADQUAT™ MC).

According to a more particular aspect, a subject of the invention is the polyelectrolyte as previously defined, for which the monomeric units resulting from at least one cationic monomer result from the following quaternary ammonium salts:

N,N,N-trimethyl-3-[(1-oxo-2-propenyl)amino]propanammonium chloride (APTAC), or

N,N,N-trimethyl-2-[(2-methyl-1-oxo-2-propenyl)]ethanammonium chloride (MADQUAT™ MC).

According to one particular aspect, a subject of the invention is a linear, branched or crosslinked polyelectrolyte in which the unit molar proportion of monomeric units resulting from at least one cationic monomer is less than or equal to 95%.

According to another particular aspect of the present invention, the polyelectrolyte as defined above is characterized in that the molar proportion of monomeric units resulting from the cationic monomer(s) is between 50.00 mol % and 95.00 mol %, more particularly between 60.00 mol % and 90.00 mol %.

The expression "monomer comprising a weak acid function" denotes principally a monomer comprising a carboxylic acid function.

According to another particular aspect, a subject of the invention is the polyelectrolyte as previously defined, for which the monomeric units resulting from at least one monomer comprising a free or partially or totally salified weak acid function result from the following free or partially or totally salified carboxylic acids:
acrylic acid,
methacrylic acid,
itaconic acid,
maleic acid, or
3-methyl-3-[(1-oxo-2-propenyl)amino]butanoic acid.

According to a more particular aspect, it is acrylic acid or methacrylic acid.

According to a quite particular aspect of the present invention, said monomer having a weak acid function is acrylic acid.

According to one particular aspect of the present invention, the polyelectrolyte as defined above is characterized in that the molar proportion of monomeric units comprising a partially or totally salified weak acid function is between 5 mol % and 50.00 mol %, more particularly less than or equal to 40% and in particularly less than or equal to 35%.

According to another particular aspect, a subject of the invention is a linear, branched or crosslinked polyelectrolyte in which the molar proportion of monomeric units comprising a free or partially or totally salified weak acid function, resulting from at least one cationic monomer is greater than or equal to 5%.

For the monomers comprising a weak acid function, the term "salified" indicates that it is principally an alkali metal salt, such as the sodium or potassium salt, or the salt of nitrogenous bases or the ammonium salt.

A subject of the invention is more particularly a linear, branched or crosslinked polyelectrolyte as previously defined, resulting from the polymerization, for 100 mol %:
a) of a molar proportion greater than or equal to 60% and less than or equal to 90% of monomeric units resulting from N,N,N-trimethyl-2-[(2-methyl-1-oxo-2-propenyl)]ethanammonium chloride, and
b) of a molar proportion greater than or equal to 10% and less than or equal to 40% of monomeric units resulting from free or partially salified acrylic acid, and
d) optionally of a molar proportion greater than 0% and less than or equal to 1% of a diethylene or polyethylene crosslinking monomer.

A subject of the invention is also more particularly a linear, branched or crosslinked polyelectrolyte as previously defined, resulting from the polymerization, for 100 mol %:
a) of a molar proportion greater than or equal to 50% and less than or equal to 90% of monomeric units resulting from at least one cationic monomer,
b) of a molar proportion greater than or equal to 1% and less than or equal to 50% of monomeric units resulting from at least one monomer comprising a free or partially or totally salified weak acid function,
c) of a molar proportion of greater than or equal to 0.05% and less than or equal to 5%, and more particularly greater than or equal to 0.1 mol % and less than or equal to 1 mol %, of monomeric units resulting from at least one monomer of formula (I),
d) optionally of a molar proportion greater than 0% and less than or equal to 1% of a diethylene or polyethylene crosslinking monomer.

In formula (I) as previously defined, the divalent radical:

represents in particular:
either a chain composed only of ethoxyl groups ($R_1$=H; n>0),
or a chain composed only of propoxyl groups ($R_1$=$CH_3$; n>0),
or a chain composed only of butoxyl groups ($R_1$=$C_2H_5$; n>0),
or a chain composed of at least two different groups chosen from ethoxyl, propoxyl and/or butoxyl groups.

When this chain is composed of different groups, they are distributed all along this chain in block or random fashion.

The expression "saturated or unsaturated, linear hydrocarbon-based aliphatic radical comprising from 8 to 30 carbon atoms" denotes more particularly for R, in formula (I) as previously defined:
either a radical derived from linear primary alcohols, for instance those derived from octyl, pelargonic, decyl, undecyl, undecenyl, lauryl, tridecyl, myristyl, pentadecyl, cetyl, heptadecyl, stearyl, oleyl, linoleyl, nonadecyl, arachidyl, behenyl, erucyl or 1-triacontanoyl alcohols. These are then octyl, nonyl, decyl, undecyl, 10-undecenyl, dodecyl, tridecyl, tetradecyl, pentadecyl, hexadecyl, heptadecyl, octadecyl, 9-octadecenyl, 10,12-octadecadienyl, 13-docosenyl or triacontanyl radicals;
or a radical derived from Guerbet alcohols, which are branched 1-alkanols corresponding to the general formula:

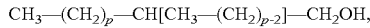

in which p represents an integer between 2 and 14, for instance 2-ethylhexyl, 2-propylheptyl, 2-butyloctyl, 2-pentylnonyl, 2-hexyldecyl or 2-octyldodecyl radicals;
or a radical derived from isoalkanols corresponding to the general formula:

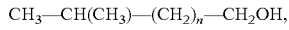

in which m represents an integer between 2 and 26, for instance 4-methylpentyl, 5-methylhexyl, 6-methylheptyl, 15-methylpentadecyl or 16-methyl-heptadecyl radicals;
or the 2-hexyloctyl, 2-octyldecyl or 2-hexyl-dodecyl radicals.

The expression "linear or branched, saturated or unsaturated hydrocarbon-based aliphatic radical comprising from 8 to 30 carbon atoms" denotes more particularly for R, in formula (I) as previously defined, an alkyl radical comprising from 12 to 22 carbon atoms.

In formula (I) as previously defined, n represents more particularly a number between 4 and 25.

In formula (I) as previously defined, A represents more particularly the vinyl radical ($CH_2$=CH—) or the isopropenyl radical [$CH_2$=C($CH_3$)—].

According to a quite particular aspect of the present invention, said monomer of formula (I) as previously defined is chosen from pentacosaethoxylated behenyl methacrylate, which is a compound of formula (I) as previously defined, in which R represents the docosanyl radical, A represents the isopropenyl radical, $R_1$ represents a hydrogen atom and n is equal to 25; tetraethoxylated lauryl acrylate, which is a compound which corresponds to formula (I) as previously defined, in which R represents the dodecyl radical, A represents the vinyl radical, $R_1$ represents a hydrogen atom and n is equal to 4; eicosaethoxylated stearyl methacrylate, which is a compound of formula (I) as previously defined, in which R represents the stearyl radical, A represents the isopropenyl radical, $R_1$ represents a hydrogen atom and n is equal to 20; or tetraethoxylated lauryl methacrylate, which is a compound which corresponds to formula (I) as previously defined, in which R represents the dodecyl radical, A represents the isopropenyl radical, $R_1$ represents a hydrogen atom and n is equal to 4.

A subject of the invention is more particularly a polyelectrolyte as previously defined, resulting from the polymerization, for 100 mol %:
a) of a molar proportion greater than or equal to 60.00% and less than or equal to 90.00% of monomeric units resulting from at least one cationic monomer,
b) of a molar proportion greater than or equal to 9.95% and less than or equal to 35.00% of monomeric units resulting from at least one monomer comprising a free or partially or totally salified weak acid function, and
c) of a molar proportion greater than or equal to 0.05% and less than or equal to 5.00 mol % of monomeric units resulting from the compound of formula (I) as previously defined.

A subject of the invention is also quite particularly a polyelectrolyte as defined previously, resulting from the polymerization, for 100 mol %:
a) of a molar proportion greater than or equal to 60.00% and less than or equal to 90.00% of monomeric units resulting from N,N,N-trimethyl-2-[(2-methyl-1-oxo-2-propenyl)]ethanammonium chloride,
b) of a molar proportion greater than or equal to 9.95% and less than or equal to 35% of monomeric units resulting from free or partially salified acrylic acid, and
c) of a molar proportion greater than or equal to 0.05% and less than or equal to 5.00% of monomeric units resulting from pentacosaethoxylated behenyl methacrylate.

According to another particular aspect of the present invention, the polyelectrolyte as defined above is cross linked.

According to the latter aspect, the crosslinking agent is chosen in particular from diethylene or polyethylene compounds, and quite particularly from diallyloxyacetic acid or a salt thereof and in particular the sodium salt thereof, triallylamine, trimethylolpropane triacrylate, ethylene glycol dimethacrylate, diethylene glycol diacrylate, diallylurea or methylene-bis(acrylamide).

According to a quite particular aspect of the present invention, the crosslinking agent used is methylene-bis(acrylamide) or trimethylolpropane triacrylate.

The crosslinking agent is then generally used in the molar proportion, expressed relative to the monomers used, of from 0.005 mol % to 1 mol %, in particular from 0.01 mol % to 0.2 mol % and more particularly from 0.01 mol % to 0.1 mol %.

A subject of the present invention is also quite particularly a polyelectrolyte as previously defined, resulting from the polymerization, for 100 mol %:

a) of a molar proportion greater than or equal to 60.00% and less than or equal to 90.00% of monomeric units resulting from N,N,N-trimethyl-2-[(2-methyl-1-oxo-2-propenyl)]ethanammonium chloride,
b) of a molar proportion greater than or equal to 9.90% and less than or equal to 35% of monomeric units resulting from free or partially salified acrylic acid,
c) of a molar proportion greater than or equal to 0.05% and less than or equal to 5.00% of monomeric units resulting from pentacosaethoxylated behenyl methacrylate, and
d) of a proportion greater than or equal to 0.005 mol % and less than 1 mol % of trimethylolpropane triacrylate.

According to another aspect of the present invention, a subject of the invention is a process for preparing a polyelectrolyte as previously defined, comprising the following successive steps:

A step a) of preparing a reaction mixture comprising, in the desired molar proportions and in a solvent (S), monomeric units resulting from at least one cationic monomer, monomeric units resulting from at least one monomer comprising a free or partially or totally salified weak acid function, and optionally monomeric units resulting from at least one monomer of formula (I) as previously defined, and, if necessary or if desired, the crosslinking and/or the other additives, said solvent (S) being:

either a ketone of formula (II):

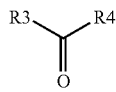

in which R3 and R4, which may be identical or different, represent, independently of one another, a methyl radical, an ethyl radical, an isopropyl radical or an isobutyl radical;
or a mixture consisting of, for 100 mol %:
water in a proportion greater than 0 mol % and less than or equal to 25 mol %; and
a ketone of formula (II) as defined above, in a proportion greater than or equal to 75 mol % and less than 100%;

A step b) during which the polymerization reaction is initiated by introducing into said reaction mixture prepared in step a) a free-radical initiator, and is then left to take place to its conclusion, so as to obtain a precipitate of said linear polyelectrolyte.

According to another particular aspect of the present invention, in step b) of the process as previously defined, the polymerization reaction is initiated at a temperature greater than or equal to 50° C. using a radical initiator which produced radicals by homolysis, such as dilauroyl peroxide, azobis(isobutyronitrile) or else azo derivatives.

According to another particular aspect of the present invention, in step b) of the process as previously defined, the polymerization reaction is initiated by an oxidation/reduction couple such as an oxidation/reduction couple which generates hydrogen sulfite ($HSO_3$) ions, for instance the cumene hydroperoxide/sodium metabisulfite ($Na_2S_2O_5$) couple or the cumene hydroperoxide/thionyl chloride ($SOCl_2$) couple, at a temperature of less than or equal to 20° C., if desired accompanied by a polymerization coinitiator, for instance azobis(isobutyronitrile), dilauryl peroxide of sodium persulfate, and then carried out quasiadiabatically.

According to another particular aspect of the present invention, in step b) of the process as previously defined, the polymerization reaction is initiated at a temperature greater than or equal to 50° C. using a radical initiator which produces radicals by homolysis, such as dilauryl peroxide, azobis(isobutyronitrile) or else azo derivatives.

The process as defined above can also comprise a step c) of isolating said precipitate obtained in step b) by separation from said solvent (S), and then, if necessary or if desired, in step d) of drying said precipitate resulting from step c).

According to another particular aspect of the present invention, in step c) of the process as previously defined, the separation of the precipitate obtained from said organic solvent is carried out by filtration.

According to another particular aspect, a subject of the present invention is a process as defined above, in which said solvent (S) is:
either a ketone chosen from propan-2-one, butan-2-one, pentan-2-one, 3-methylbutan-2-one, 3-ethylpentan-20-one or 4-methylpentan-2-one;
or a mixture consisting of, for 100 mol %:
water in a proportion greater than 0 mol % and less than or equal to 10 mol %, preferably less than or equal to 5 mol %; and
a ketone chosen from propan-2-one, butan-2-one, pentan-2-one, 3-methylbutan-2-one, 3-ethylpentan-2-one or 4-methylpentan-2-one, of formula (II) as previously defined, in a molar proportion greater than or equal to 90 mol %, preferably greater than or equal to 95 mol %, and less than 100 mol %.

According to a quite particular aspect, a subject of the invention is the process as defined above, in which said solvent (S) is either acetone, or a water-acetate mixture in a water/acetone molar ratio greater than 0 and less than or equal to 5/95.

By virtue of its cationic nature, the polyelectrolyte which is the subject of the present invention is advantageously used as a thickener and/or as an emulsifier in cosmetic or pharmaceutical compositions intended for hair care and/or hair conditioning.

Consequently, according to another aspect, a subject of the invention is the use of the polyelectrolyte as previously defined, as a thickener and/or as an emulsifier in cosmetic or pharmaceutical compositions and more particularly those intended for hair care and/or hair conditioning.

The polyelectrolyte which is a subject of the present invention can be formulated in cosmetic or pharmaceutical formulae such as mousses, gels, lotions, sprays, shampoos, conditioners, hand and body lotions, and sunscreens, and more generally in care products.

In the case of hair treatment or upkeep, such cosmetic or pharmaceutical compositions are usually in the form of shampoos, of emulsions, of microemulsions and, in particular in the case of conditioners, of vaporizable emulsions.

According to a final aspect, a subject of the invention is a cosmetic or pharmaceutical composition characterized in that it contains, as emulsifier and/or thickener, an effective amount of the polyelectrolyte as previously defined.

The term "effective amount" is intended to mean a weight proportion of between approximately 0.1% and approximately 5% by weight of the polyelectrolyte as previously defined.

The following examples illustrate the present invention without, however, limiting it.

EXAMPLE 1

Preparation of an acrylic acid/MADQUAT/BEM-25 terpolymer Partially Salified in Sodium Salt Form (Compound 1)

a) The following are successively added to a beaker containing 400 g of acetone:

6.63 g of acrylic acid;

7.75 g of sodium hydrogen carbonate;

242.4 g of a commercial solution containing 75% of N,N,N-trimethyl-2-[(1-oxo-2-propenyl)amino]-ethanammonium chloride (MADQUAT MC 75™);

0.58 g of pentacosaethoxylated behenyl methacrylate (BEM-25).

b) The whole mixture is left to stir with nitrogen sparging for 45 minutes, and heated to 55° C., and then 0.75 g of dilauryl peroxide is added in order to initiate the polymerization reaction.

After two of reflux, the reaction medium is cooled.

c) The precipitate obtained is filtered off and then dried under vacuum. The expected polymer is obtained in powder form.

The viscosimetric properties of the polymer powder obtained are the following:

Viscosity at 25° C. of an aqueous dispersion comprising 2% by weight of the powder obtained: 25 280 mPa·s (Brookfield RVT, spindle 6, rotational speed 5).

Viscosity of an aqueous dispersion comprising 2% by weight of the powder obtained and 0.1% by weight of sodium chloride: 11 800 mPa·s (Brookfield RVT, spindle 3, rotational speed 5).

EXAMPLE 2

Preparation of an Acrylic Acid/MADQUAT/BEM-25 Terpolymer Partially Salified in Sodium Salt Form, Crosslinked with Trimethylolpropane Triacrylate (Compound 2)

a) The following are successively added to a beaker containing 400 g of acetone:

6.63 g of acrylic acid;

7.75 g of sodium hydrogen carbonate;

242.4 g of a commercial solution containing 75% of N,N,N-trimethyl-2-[(1-oxo-2-propenyl)amino]-ethanammonium chloride (MADQUAT MC 75™);

0.58 g of pentacosaethoxylated behenyl methacrylate (BEM-25), and 0.16 g of trimethylolpropane triacrylate.

b) The whole mixture is left to stir with nitrogen sparging for 45 minutes, and heated to 55° C., and then 0.75 g of dilauryl peroxide is added in order to initiate the polymerization reaction.

After two of reflux, the reaction medium is cooled.

c) The precipitate obtained is filtered off and then dried under vacuum. The expected polymer is obtained in the form of a powder.

The viscosimetric properties of the polymer powder obtained are the following:

Viscosity at 25° C. of an aqueous dispersion comprising 2% by weight of the powder obtained: 19 920 mPa·s (Brookfield RVT, spindle 6, rotational speed 5).

Viscosity of an aqueous dispersion comprising 2% by weight of the powder obtained and 0.1% by weight of sodium chloride: 7 740 mPa·s (Brookfield RVT, spindle 3, rotational speed 5).

EXAMPLE 3

Antistress Hair Care Product

| Formula | |
|---|---|
| Phase A | |
| Water: | QS 100% |
| Xanthan gum | 0.50% |
| Phase B | |
| Sepicap ™ MP: | 3.00% |
| Phase C | |
| Compound 1: | 4.00% |
| Phase D | |
| Butylene glycol: | 5.00% |
| Lanol ™ 99: | 5.00% |
| Sepicide ™ HB: | 0.30% |
| Sepicide ™ CI: | 0.20% |
| Fragrance | 0.20% |

Procedure

Disperse the xanthan gum in the water with a deflocculator. Then add Sepicap™ MP, and then compound 1; disperse it and then add the ingredients of phase D.

EXAMPLE 4

Restructuring Cream Mask for Stressed and Embrittled Hair

| Formula | |
|---|---|
| Phase A | |
| Montanov ™ 82: | 3.00% |
| Lanol ™ P: | 6.00% |
| Amonyl ™ MD: | 1.00% |
| Isostearyl isononanoate | 5.00% |
| Compound 2: | 2.50% |
| Phase B | |
| Water: | QS 100% |
| Phase C | |
| Sepicap ™ MP: | 3.00% |
| Sepicide ™ HB: | 0.30% |
| Sepicide ™ CI: | 0.20% |

Procedure

Melt phase A at 75° C. Heat phase B at 75° C. Emulsify A in B. At about 40° C., introduce the constituents of phase C.

EXAMPLE 5

Purifying Facial Gel

| Formula | |
|---|---|
| Phase A | |
| Montaline ™ C 40: | 7.00% |
| Pearlescent base 2078: | 5.00% |
| Compound 1: | 2.00% |
| Phase B | |
| Water: | QS 100% |

EXAMPLE 6

Coloring Shampoo

| Formula | |
|---|---|
| Phase A | |
| Montaline ™ C 40: | 15.00% |
| Disodium cocoamphoacetate: | 5.00% |
| Cetrimonium chloride: | 1.00% |
| Sepiperl ™ N: | 3.00% |
| Compound 1: | 3.00% |
| Phase B | |
| Color | QS |
| Water: | QS 100% |

EXAMPLE 7

Fluid Emulsion at Alkaline pH

| | |
|---|---|
| Marcol ™ 82: | 5.0% |
| Sodium hydroxide: | 10.0% |
| Water: | q.s. 100% |
| Compound 2: | 1.5% |

EXAMPLE 8

Restructuring Rinse-Off Cream Mask for Stressed and Embrittled Hair

| | |
|---|---|
| Ketrol ™ T: | 0.5% |
| Pecosil ™ SPP50: | 0.75% |
| N-cocoyl amino acids: | 0.70% |
| Butylene glycol: | 3.0% |
| Compound 1: | 3.0% |
| Montanov ™ 82: | 3.0% |
| Jojoba oil: | 1.0% |
| Lanol ™ P: | 6.0% |
| Amonyl ™ DM: | 1.0% |
| Lanol ™ 99: | 5.0% |
| Sepicide ™ HB: | 0.3% |
| Sepicide ™ CI: | 0.2% |
| Fragrance: | 0.2% |
| Water: | qs. 100% |

EXAMPLE 9

Hair Lotion

| | |
|---|---|
| Butylene glycol: | 3.0% |
| Compound 1: | 3.0% |
| Simulsol ™ 1293: | 3.0% |
| Lactic acid: | qs. pH = 6 |
| Sepicide ™ HB: | 0.2% |
| Sepicide ™ CI: | 0.3% |
| Fragrance: | 0.3% |
| Water: | qs. 100% |

EXAMPLE 10

Protecting and Relaxing Shampoo

| | |
|---|---|
| Amonyl ™ 675 SB: | 5.00% |
| Sodium lauroyl ether sulfate at 28%: | 35.0% |
| Compound 2: | 3.0% |
| Sepicide ™ HB: | 0.5% |
| Sepicide ™ CI: | 0.3% |
| Sodium hydroxide: | q.s. pH = 7.2 |
| Fragrance: | 0.3% |
| Dye (FDC blue 1/yellow 5) | q.s. |
| Water: | qs. 100% |

EXAMPLE 11

Leave-On Protector; Antistress Hair Care Product

| | |
|---|---|
| Ketrol ™ T: | 0.5% |
| Mixture of cocoyl amino acids: | 3.0% |
| Butylene glycol: | 5.0% |
| DC 1501: | 5.0% |
| Compound 1: | 4.0% |
| Sepicide ™ HB: | 0.5% |
| Sepicide ™ CI: | 0.3% |
| Fragrance: | 0.3% |
| Water: | qs. 100% |

The definitions of the commercial products used in the examples are the following:

Montaline™ (cocoammoniumcarbamoyl chloride) sold C40: by SEPPIC.

Sepiperl™ N: (cocoyl glucoside/cocoyl alcohol) sold by SEPPIC.

Amonyl™ DM: (quaternium 82) sold by SEPPIC.

Sepicap™ MP: (sodium cocoyl amino acids/potassium dimethicone copolyol panthenyl phosphate) sold by SEPPIC.

Simulsol™ 1293 is hydrogenated and ethoxylated castor oil, with an ethoxylation number equal to 40, sold by the company SEPPIC.

Ketrorl™ T is xanthan gum sold by the company Kelco.

Lanol™ 99 is isononyl isononanoate sold by the company SEPPIC.

DC 1501™ is a mixture of cyclopentasiloxane and dimethiconol, sold by the company Dow Chemical.

Montanov™ 82 is an emulsifier based on cetearyl alcohol and cocoyl glucoside.

Sepicide™ CI imidazolidene urea, is a preservative sold by the company SEPPIC.

Sepicide™ HB which is a mixture of phenoxyethanol, methylparaben, ethylparaben, propyl-paraben and butylparaben, is a preservative sold by the company SEPPIC.

Lanol™ P is an additive with a stabilizing effect, sold by the company SEPPIC.

The invention claimed is:

1. A linear, branched or crosslinked polyelectrolyte resulting from the polymerization, for 100 mol %:
   a) of a molar proportion greater than or equal to 60.00% and less than or equal to 90.00% of monomeric units resulting from at least one cationic monomer selected from the group consisting of:
   N,N,N-trimethyl-3-[(2-methyl-1-oxo-2-propenyl) amino]propanammonium chloride;
   N,N,N-trimethyl-3-[(1-oxo-2-propenyl)amino]-propanammonium chloride;
   diallyldimethylammonium chloride;
   N,N,N-trimethyl-2-[(1-oxo-2-propenyl)]ethanammonium chloride; and
   N,N,N-trimethyl-2-[(2-methyl-1-oxo-2-propenyl)]-ethanammonium chloride,
   b) of a molar proportion greater than or equal to 9.95% and less than or equal to 35.00% of monomeric units resulting from at least one monomer comprising a free or partially or totally salified carboxylic acid function selected from the group consisting of acrylic acid, methacrylic acid, itaconic acid, maleic acid, and 3-methyl-3-[(1-oxo-2-propenyl)amino]butanoic acid,
   c) of a molar proportion greater than or equal to 0.05% and less than or equal to 5.00 mol % of monomeric units resulting from at least one monomer of formula (I):

$$A-C(=O)-O-[(CH_2-CH(R_1)-O]_n-R \qquad (I)$$
   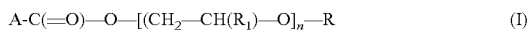

in which n represents, independently, a number between 1 and 50, A represents an unsaturated aliphatic monovalent radical comprising from 2 to 6 carbon atoms, $R_1$ represents a hydrogen atom, a methyl radical or an ethyl radical and R represents a linear or branched, saturated or unsaturated hydrocarbon-based aliphatic radical comprising from 8 to 30 carbon atoms, and
   d) optionally of a molar proportion greater than 0% and less than or equal to 1% of a diethylene or polyethylene crosslinking monomer.

2. The polyelectrolyte as defined in claim 1, for which the monomeric units resulting from at least one cationic monomer result from the following quaternary ammonium salts:
   N,N,N-trimethyl-3-[(1-oxo-2-propenyl)amino]-propanammonium chloride, or
   N,N,N-trimethyl-2-[(2-methyl-1-oxo-2-propenyl)]ethanammonium chloride.

3. The polyelectrolyte as defined in claim 1, for which the monomeric units resulting from at least one monomer comprising a free or partially or totally salified carboxylic acid function result from acrylic acid or from methacrylic acid.

4. The polyelectrolyte as defined in claim 3, resulting from the polymerization, for 100 mol %:
   a) of a molar proportion greater than or equal to 60.00% and less than or equal to 90.00% of monomeric units resulting from N,N,N-trimethyl-2-[(2-methyl-1-oxo-2-propenyl)]ethanammonium chloride, and
   b) of a molar proportion greater than or equal to 9.95% and less than or equal to 35.00% of monomeric units resulting from free or partially salified acrylic acid,
   c) of a molar proportion greater than or equal to 0.05% and less than or equal to 5.00 mol % of monomeric units resulting from at least one monomer of formula (I):

$$A-C(=O)-O-[(CH_2-CH(R_1)-O]_n-R \qquad (I)$$
   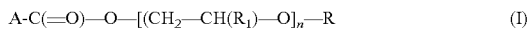

in which n represents, independently, a number between 1 and 50, A represents an unsaturated aliphatic monovalent radical comprising from 2 to 6 carbon atoms, $R_1$ represents a hydrogen atom, a methyl radical or an ethyl radical and R represents a linear or branched, saturated or unsaturated hydrocarbon-based aliphatic radical comprising from 8 to 30 carbon atoms, and
   d) optionally a molar proportion greater than 0% and less than or equal to 1% of a diethylene or polyethylene crosslinking monomer.

5. The linear, branched or crosslinked polyelectrolyte as defined in claim 1, resulting from the polymerization, for 100 mol %:

a) of a molar proportion greater than or equal to 60.00% and less than or equal to 90.00% of monomeric units resulting from at least one cationic monomer selected from the group consisting of:
N,N,N-trimethyl-3-[(2-methyl-1-oxo-2-propenyl)amino]propanammonium chloride;
N,N,N-trimethyl-3-[(1-oxo-2-propenyl)amino]-propanammonium chloride;
diallyldimethylammonium chloride;
N,N,N-trimethyl-2-[(1-oxo-2-propenyl)]ethanammonium chloride; and
N,N,N-trimethyl-2-[(2-methyl-1-oxo-2-propenyl)]-ethanammonium chloride,
b) of a molar proportion greater than or equal to 9.95% and less than or equal to 35.00% of monomeric units resulting from at least one monomer comprising a free or partially or totally salified carboxylic acid function selected from the group consisting of acrylic acid, methacrylic acid, itaconic acid, maleic acid, and 3-methyl-3-[(1-oxo-2-propenyl)amino]butanoic acid,
c) of a molar proportion of greater than or equal to 0.1% and less than or equal to 1% of monomeric units resulting from at least one monomer of formula (I):

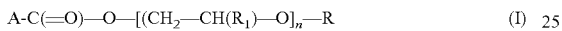

$$A-C(=O)-O-[(CH_2-CH(R_1)-O]_n-R \quad (I)$$

in which n represents, independently, a number between 1 and 50, A represents an unsaturated aliphatic monovalent radical comprising from 2 to 6 carbon atoms, $R_1$ represents a hydrogen atom, a methyl radical or an ethyl radical and R represents a linear or branched, saturated or unsaturated hydrocarbon-based aliphatic radical comprising from 8 to 30 carbon atoms, and
d) optionally of a molar proportion greater than 0% and less than or equal to 1% of a diethylene or polyethylene crosslinking monomer.

6. The polyelectrolyte as defined in claim 1, for which, in formula (I), n represents a number between 4 and 25.

7. The polyelectrolyte as defined in claim 1, for which, in formula (I), A represents the vinyl radical ($CH_2=CH-$) or the isopropenyl radical [$CH_2=C(CH_3)-$].

8. The polyelectrolyte as defined in claim 7, for which the compound of formula (I) as previously defined is chosen from:
pentacosaethoxylated behenyl methacrylate;
tetraethoxylated lauryl acrylate;
eicosaethoxylated stearyl methacrylate; or
tetraethoxylated lauryl methacrylate.

9. The polyelectrolyte as defined in claim 1, resulting from the polymerization, for 100 mol %:
a) of a molar proportion greater than or equal to 60.00% and less than or equal to 90.00% of monomeric units resulting from N,N,N-trimethyl-2-[(2-methyl-1-oxo-2-propenyl)]ethanammonium chloride,
b) of a molar proportion greater than or equal to 9.95% and less than or equal to 35% of monomeric units resulting from free or partially salified acrylic acid, and c) of a molar proportion greater than or equal to 0.05% and less than or equal to 5.00% of monomeric units resulting from pentacosaethoxylated behenyl methacrylate.

10. The polyelectrolyte as defined in claim 1, characterized in that it is crosslinked.

11. The polyelectrolyte as defined in claim 10, resulting from the polymerization, for 100 mol %:
a) of a molar proportion greater than or equal to 60.00% and less than or equal to 90.00% of monomeric units resulting from N,N,N-trimethyl-2-[(2-methyl-1-oxo-2-propenyl)]ethanammonium chloride,
b) of a molar proportion greater than or equal to 9.95% and less than or equal to 35% of monomeric units resulting from free or partially salified acrylic acid,
c) of a molar proportion greater than or equal to 0.05% and less than or equal to 5.00% of monomeric units resulting from pentacosaethoxylated behenyl methacrylate, and
d) of a proportion greater than or equal to 0.005 mol % and less than 1 mol % of trimethylolpropane triacrylate.

12. A process for preparing a polyelectrolyte as defined in claim 1, comprising the following successive steps:
A step a) of preparing a reaction mixture comprising, in the desired molar proportions and in a solvent (S), monomeric units resulting from at least one cationic monomer, monomeric units resulting from at least one monomer comprising a free or partially or totally salified weak acid function, and optionally monomeric units resulting from at least one monomer of formula (I) as previously defined, and, if necessary or if desired, the crosslinker and/or the other additives, said solvent (S) being:
either a ketone of formula (II):

in which R3 and R4, which may be identical or different, represent, independently of one another, a methyl radical, an ethyl radical, an isopropyl radical or an isobutyl radical;
or a mixture consisting of, for 100 mol %:
water in a proportion greater than 0 mol % and less than or equal to 25 mol %; and
a ketone of formula (II) as defined above, in a proportion greater than or equal to 75 mol % and less than 100%;
A step b) during which the polymerization reaction is initiated by introducing into said reaction mixture prepared in step a) a free-radical initiator, and is then left to take place to its conclusion, so as to obtain a precipitate of said polyelectrolyte.

13. A cosmetic or pharmaceutical composition characterized in that it contains, as emulsifier and/or thickener, an effective amount of the polyelectrolyte as defined in claim 1.

* * * * *